United States Patent [19]

Wilson et al.

[11] 4,310,701
[45] * Jan. 12, 1982

[54] PROCESS FOR THE PREPARATION OF HOMOLOGUES OF METHYL DIHYDROJASMONATE

[75] Inventors: Richard A. Wilson, Westfield; Braja D. Mookherjee, Holmdel; John B. Hall, Rumson; Gilbert Stork, Englewood, all of N.J.

[73] Assignee: International Flavors & Fragrances Inc., New York, N.Y.

[ * ] Notice: The portion of the term of this patent subsequent to Apr. 7, 1998, has been disclaimed.

[21] Appl. No.: 206,688

[22] Filed: Nov. 13, 1980

Related U.S. Application Data

[63] Continuation-in-part of Ser. No. 113,297, Jan. 18, 1980, Pat. No. 4,260,830.

[51] Int. Cl.³ ............................................. C07C 45/66
[52] U.S. Cl. .................................................. 568/347
[58] Field of Search ........................................ 568/347

[56] References Cited

U.S. PATENT DOCUMENTS 4,260,830  4/1981  Wilson ............................... 568/485

*Primary Examiner*—Robert Gerstl
*Attorney, Agent, or Firm*—Arthur L. Liberman

[57] ABSTRACT

A process is described for the preparation of alkyl and alkylene homologues of methyl dihydrojasmonate to one of the reaction sequences:

which incorporate the novel process step:

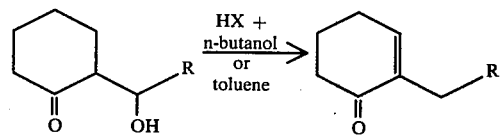

In the above reaction sequence, X is chloro or bromo and R is $C_1$-$C_4$ alkyl.

5 Claims, 10 Drawing Figures

GLC PROFILE FOR EXAMPLE I, FRACTION 2.

GLC PROFILE FOR EXAMPLE I, FRACTION 1.

GLC PROFILE FOR EXAMPLE I, FRACTION 3.

GLC PROFILE FOR EXAMPLE I, FRACTION 4.

GLC PROFILE FOR EXAMPLE I, FRACTION 6.

GLC PROFILE FOR EXAMPLE I, FRACTION 5.

GLC PROFILE FOR EXAMPLE I, FRACTION 8.

GLC PROFILE FOR EXAMPLE I, FRACTION 7.

GLC PROFILE FOR EXAMPLE I, FRACTION 10.

GLC PROFILE FOR EXAMPLE I, FRACTION 9.

PROCESS FOR THE PREPARATION OF HOMOLOGUES OF METHYL DIHYDROJASMONATE

This application is a continuation-in-part of application for U.S. Letters Patent, Ser. No. 113,297 filed on Jan. 18, 1980, now U.S. Pat. No. 4,260,830 issued on Apr. 7, 1981.

BACKGROUND OF THE INVENTION

Methyl dihydrojasmonate having the structure:

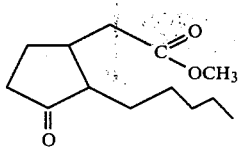

and alkyl and alkylene homologues thereof defined according to the structures:

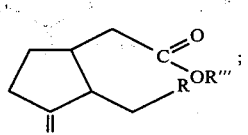

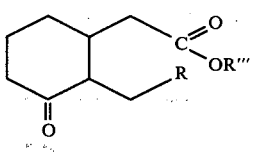

or the generic structure:

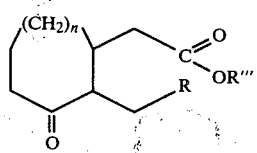

wherein n is 0 or 1 and wherein R is $C_1-C_4$ alkyl and R''' represents $C_1-C_3$ alkyl are valuable ingredients useful as medicinal drug intermediates and perfumery materials; for use in augmenting or enhancing the aroma of perfumes, perfumed articles such as nonionic, anionic, cationic or zwitterionic detergents or dryer-added fabric softener articles or colognes.

Methyl dihydrojasmonate has been previously shown to be prepared in United Kingdom Patent Specification No. 907,431 published on Oct. 3, 1962, according to the process:

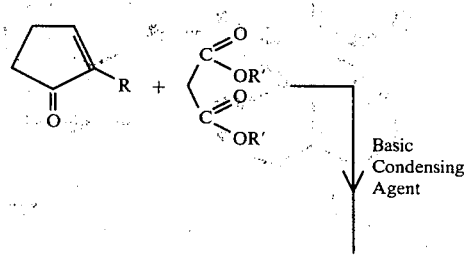

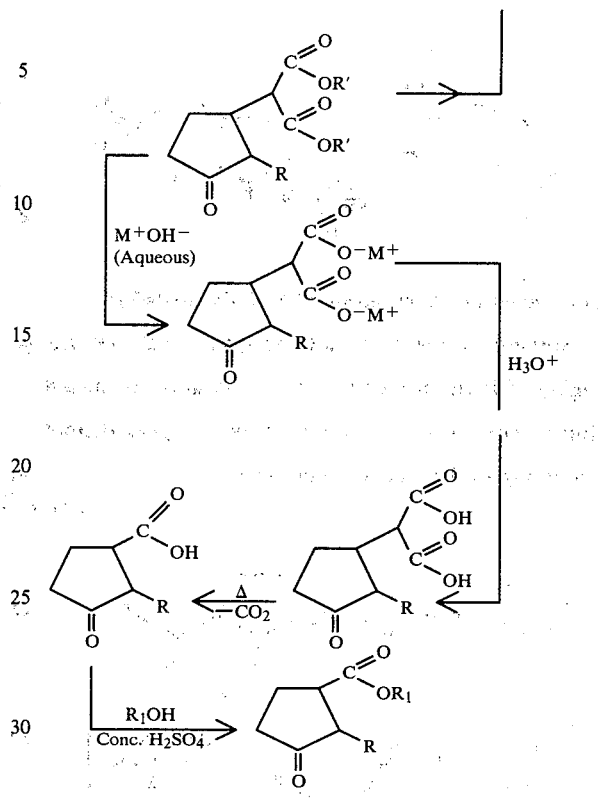

wherein R' is methyl or ethyl and R represents lower alkyl, and wherein $R_1$ represents lower alkyl and M represents alkali metal such as potassium or sodium.

Furthermore, the prior art sets forth alkylidenylation reactions with cyclopentanone and unsaturated aldehydes according to the reaction sequence:

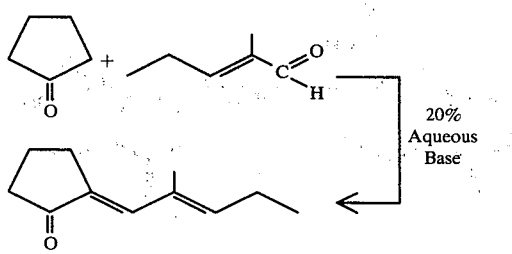

(Vol. 78 Chemical Abstracts 59537k (abstract of Mekhtiev et al, Azerb. Khim. Zh. 1973 (1), 47–51)) and the reaction:

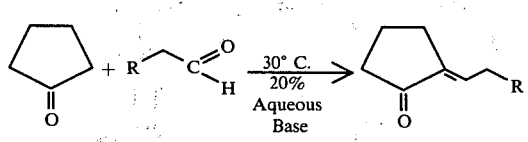

(Vol. 79 Chemical Abstracts 78170t (abstract of Mekhtiev et al, Azerb. Khim. Zh. 1972 (4), 50–5)) wherein R is propyl or isopropyl.

German Offenlengungsschrift No. 27 32 107, published on Jan. 9, 1978, sets forth the reaction:

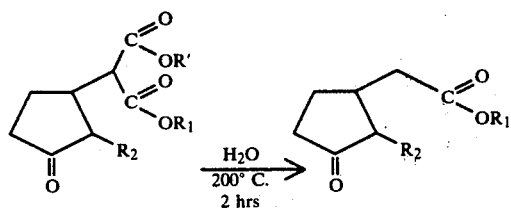
(abstracted in Chem. Abstract Vol. 88, 169667a).
Nothing in the prior art, however, indicates the highly efficient reaction sequence leading to methyl dihydrojasmonate or lower alkyl homologues thereof according to the reaction sequence:
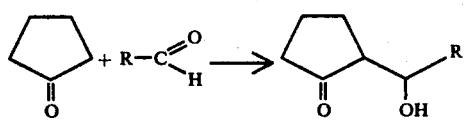
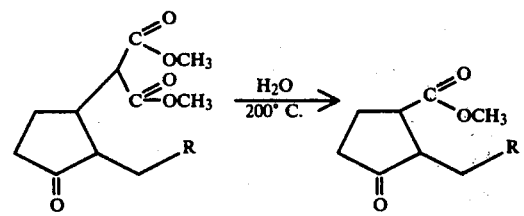
or the reaction sequence:
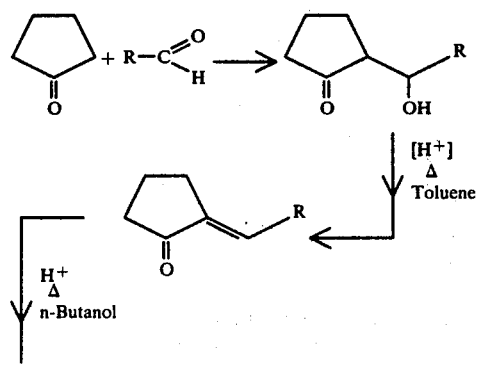
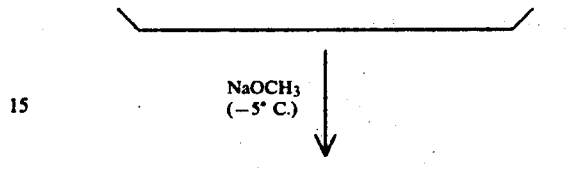
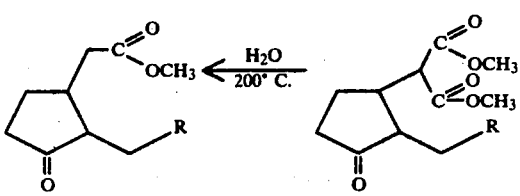
or the reaction sequence:
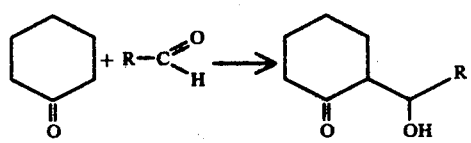
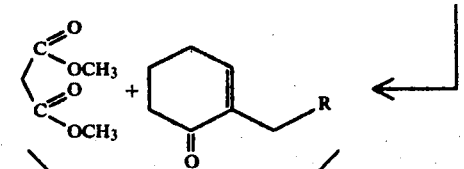
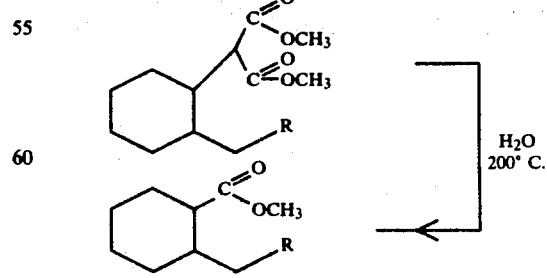
or the reaction:

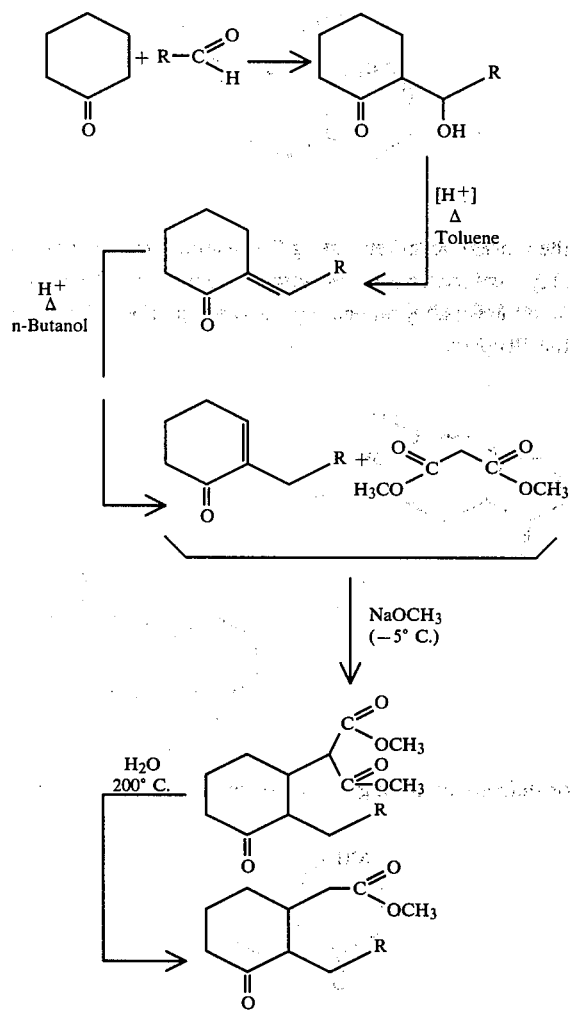

wherein R is $C_1$–$C_4$ alkyl; X is chloro or bromo; and n is 0 or 1.

THE INVENTION

Figure 2:
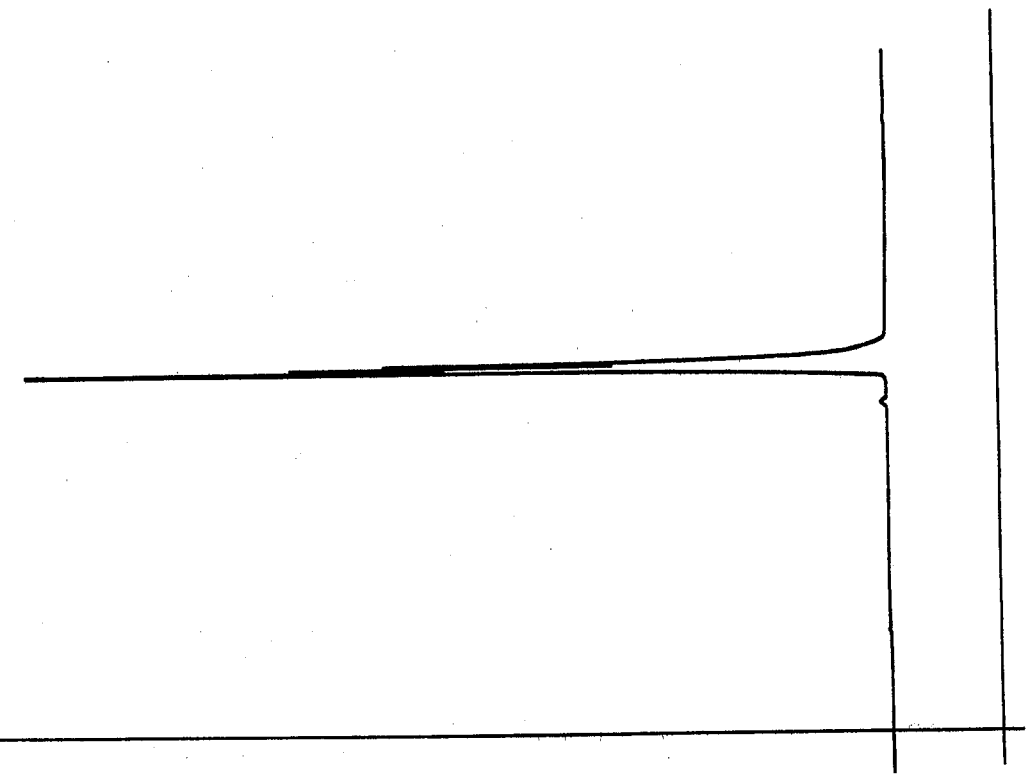
FIG. 2 represents the GLC profile for fraction 2 resulting from the fractional distillation of the reaction product produced according to Example I(D).
Figure 1:
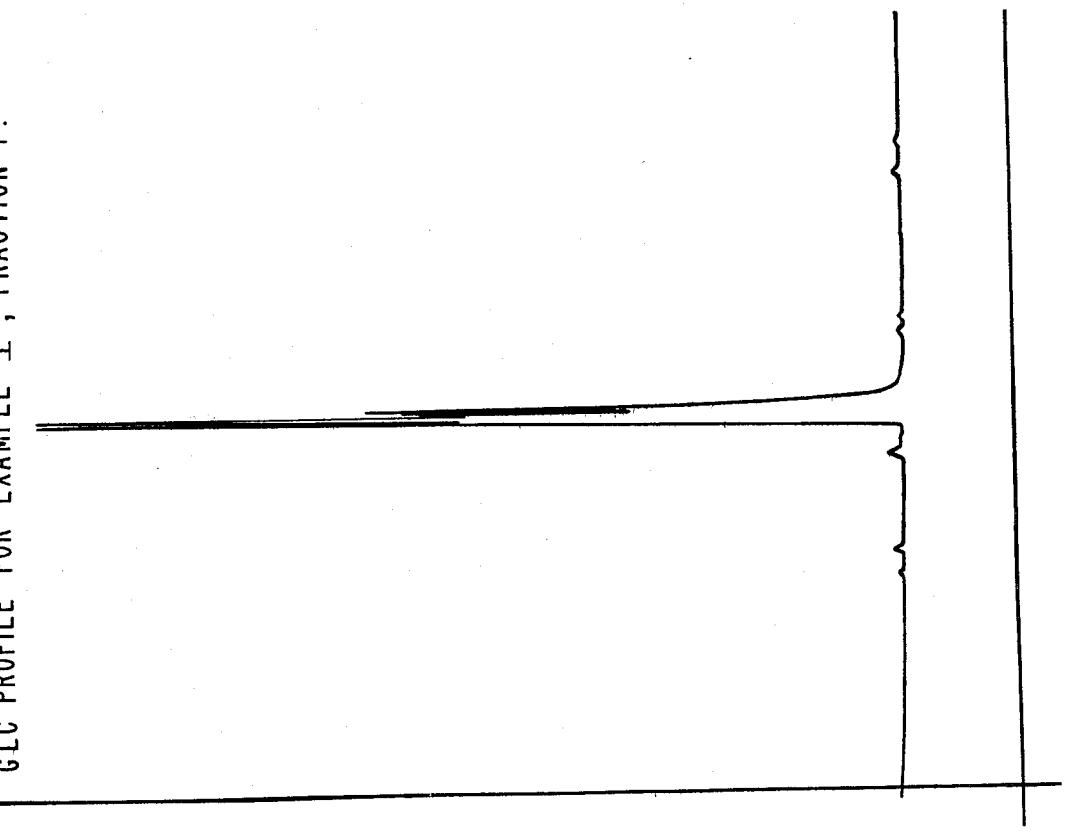
FIG. 1 represents the GLC profile for fraction 1 resulting from the fractional distillation of the reaction product produced according to Example I(D).
Figure 3:
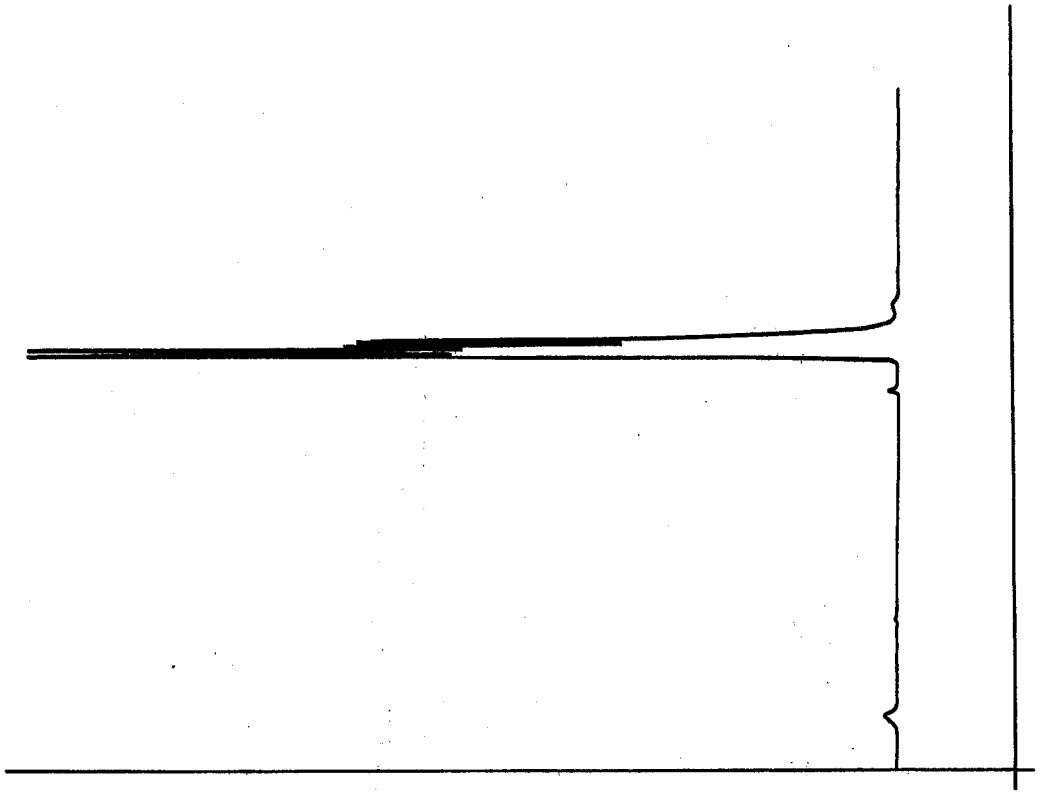
FIG. 3 represents the GLC profile for fraction 3 resulting from the fractional distillation of the reaction product produced according to Example I(D).
Figure 4:
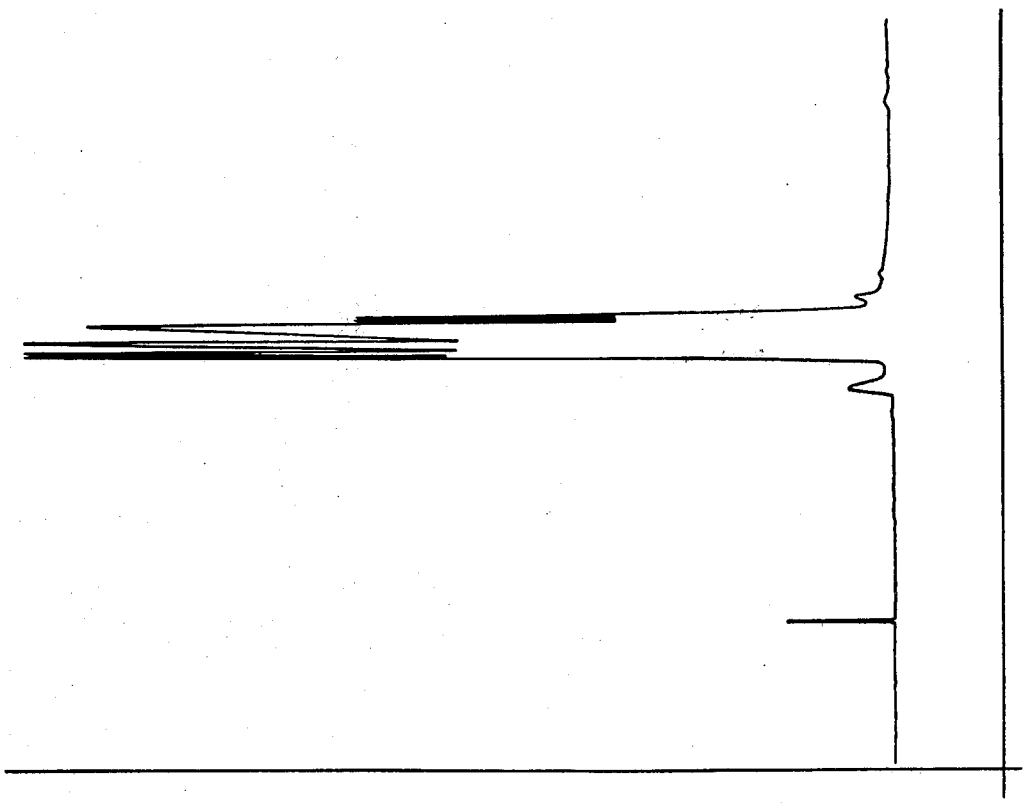
FIG. 4 represents the GLC profile for fraction 4 resulting from the fractional distillation of the reaction product produced according to Example I(D).
Figure 6:
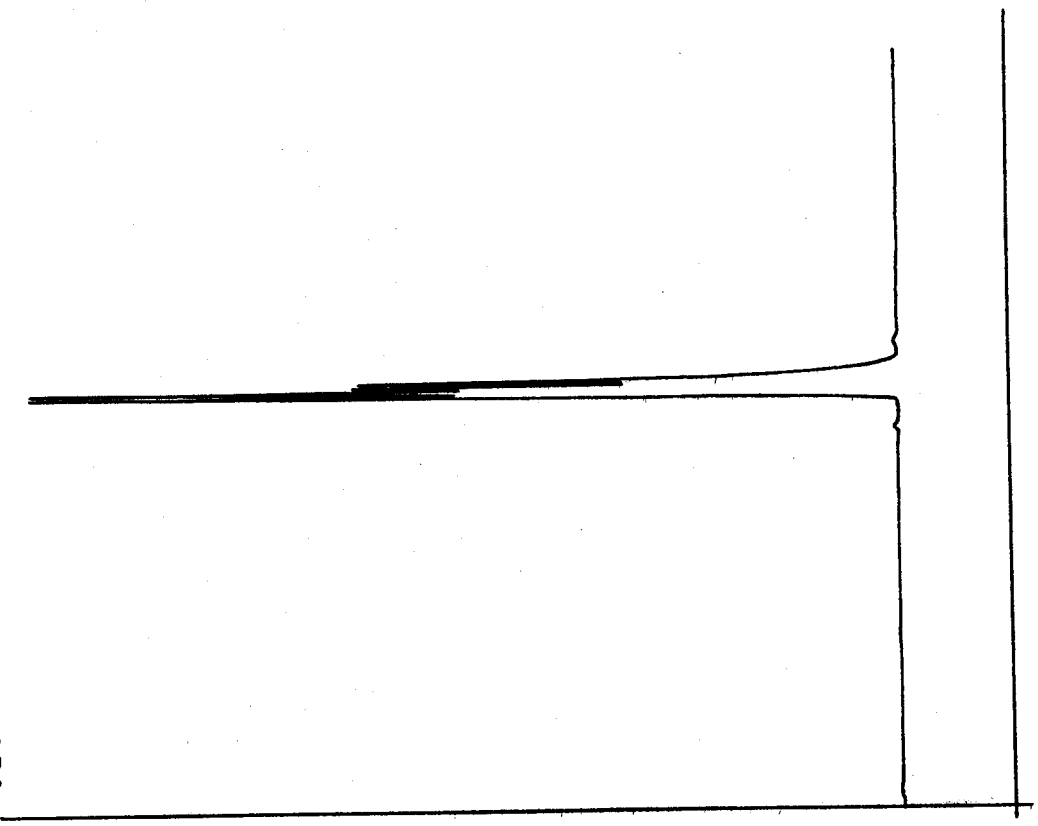
FIG. 6 represents the GLC profile for fraction 6 resulting from the fractional distillation of the reaction product produced according to Example I(D).
Figure 5:
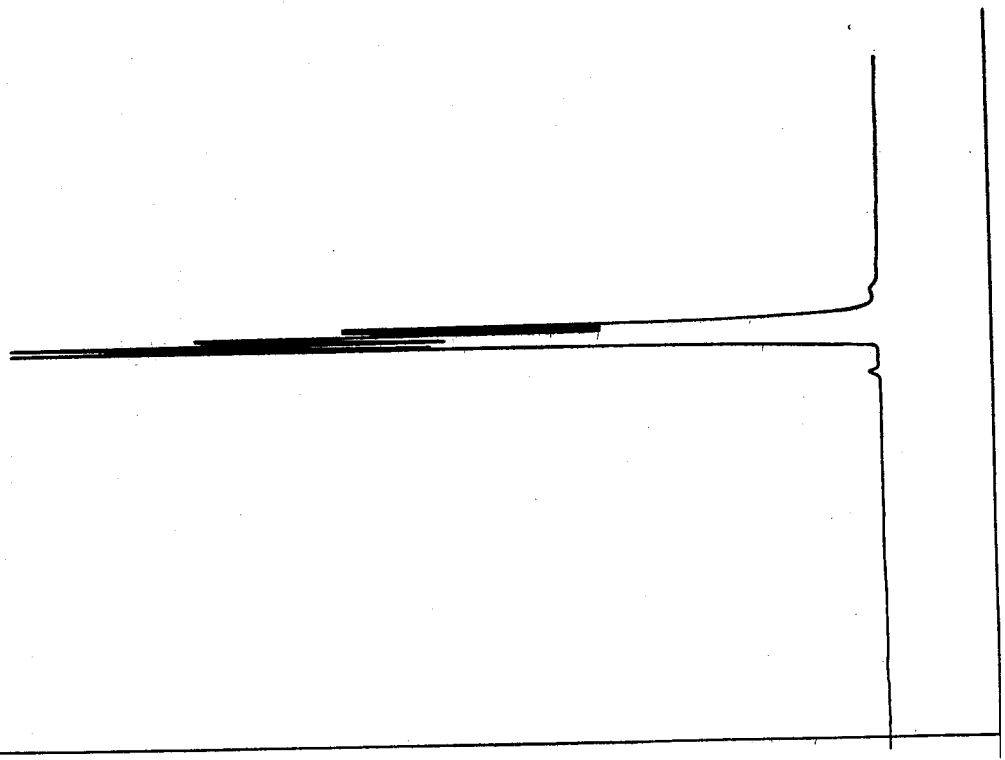
FIG. 5 represents the GLC profile for fraction 5 resulting from the fractional distillation of the reaction product produced according to Example I(D).
Figure 8:
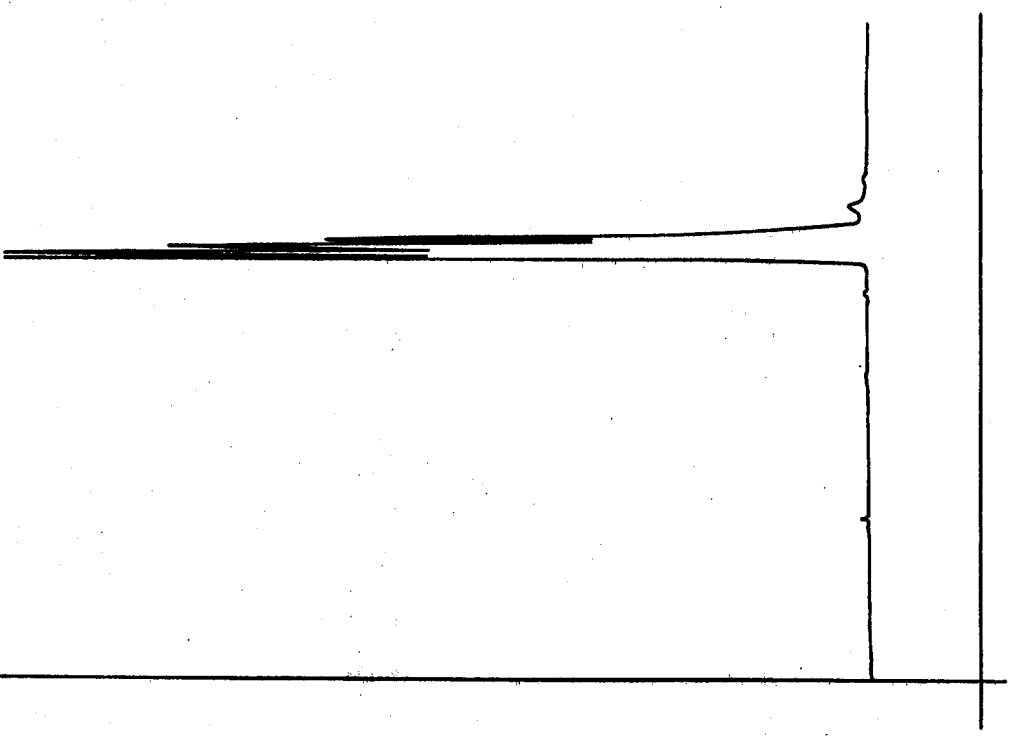
FIG. 8 represents the GLC profile for fraction 8 resulting from the fractional distillation of the reaction product produced according to Example I(D).
Figure 7:
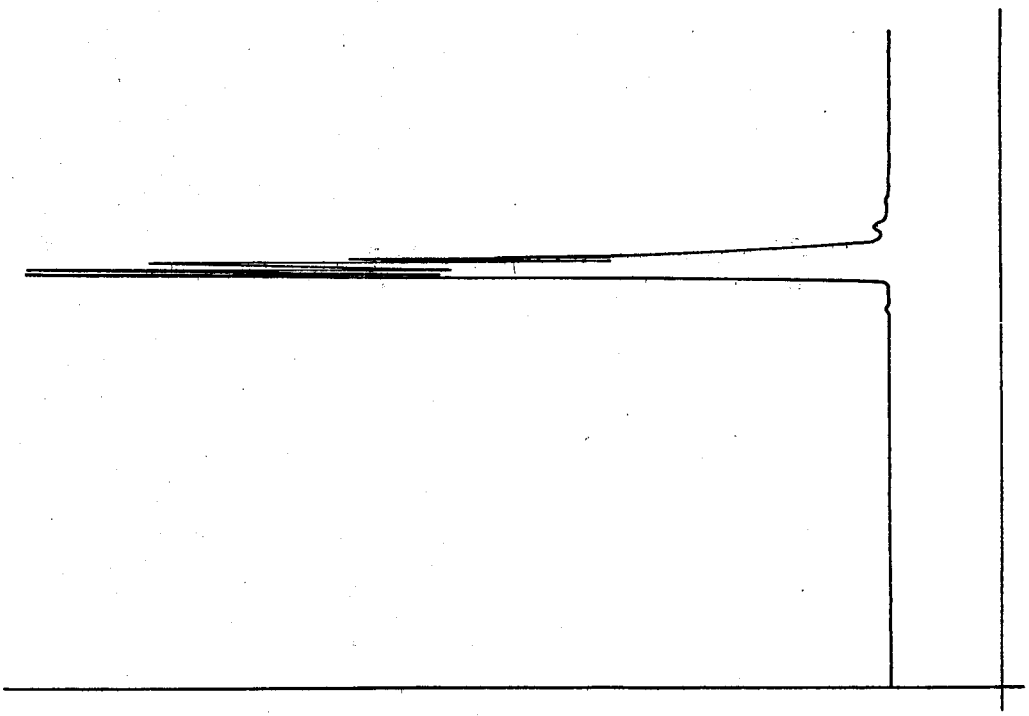
FIG. 7 represents the GLC profile for fraction 7 resulting from the fractional distillation of the reaction product produced according to Example I(D).
Figure 10:
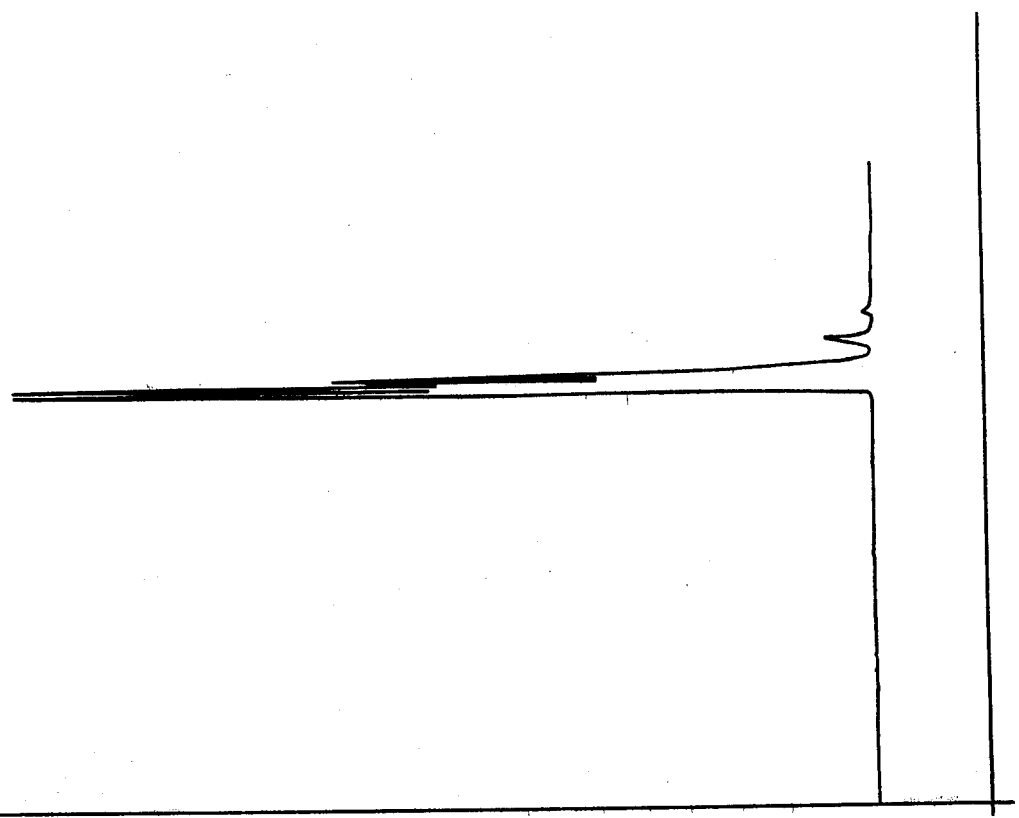
FIG. 10 represents the GLC profile for fraction 10 resulting from the fractional distillation of the reaction product produced according to Example I(D).
Figure 9:
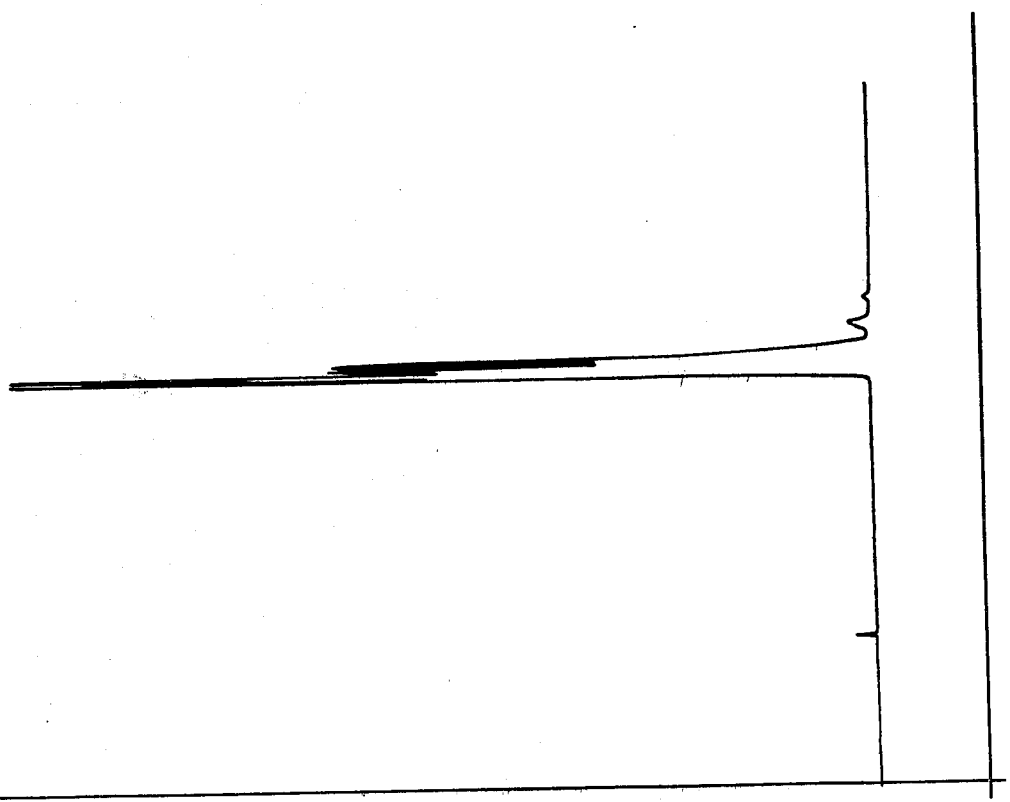
FIG. 9 represents the GLC profile for fraction 9 resulting from the fractional distillation of the reaction product produced according to Example I(D).

The invention, accordingly, comprises the novel process and steps, specific embodiments of which are also described hereinafter by use of experiments and in accordance with what is now the preferred practice of the invention.

The process of our invention comprises reacting a $C_2$–$C_5$ aldehyde having the structure:

with a cycloalkanone having the structure:

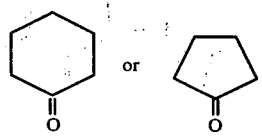

or defined according to the generic structure:

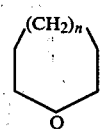

wherein n is 0 or 1, to form an aldol having the structure:

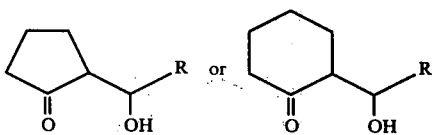

or defined according to the generic structure:

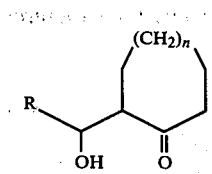

wherein R is $C_1$–$C_4$ alkyl and wherein n is 0 or 1, and then dehydrating the aldol to form the alkylidene cycloalkanone and then rearranging the thus-formed alkylidene cycloalkanone to form the alkyl cycloalkenone having the structure:

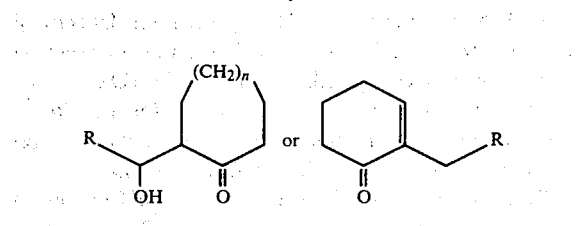

or defined according to the generic structure:

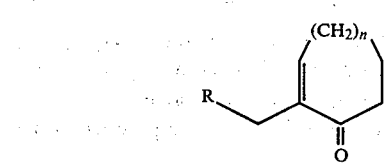

wherein R is $C_1$–$C_4$ alkyl or n is 0 or 1; or, in the alternative, simultaneously dehydrating and rearranging the aldol to form the alkyl cyclopentenone having the structure:

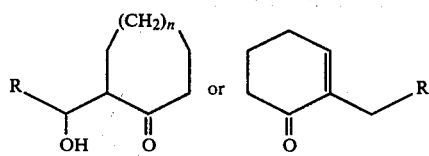

or defined according to the generic structure:

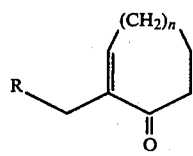

wherein R and n are as defined above, then reacting the alkylcyclopentenone with a malonic ester having the structure:

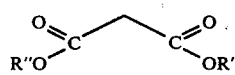

thereby forming the malonic ester alkyl cycloalkanone reaction product having the structure:

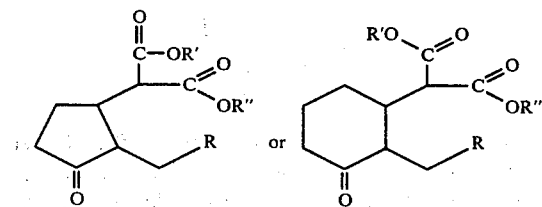

or defined according to the generic structure:

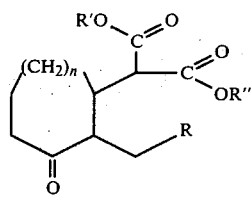

then mono-decarboxylating the resulting malonic ester-alkyl cycloalkenone reaction product to form the methyl dihydrojasmonate or homologue thereof having the structure:

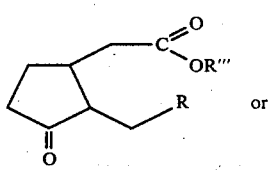

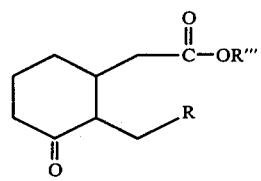

or defined according to the generic structure:

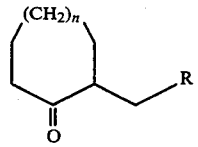

wherein n is 0 or 1 wherein R is $C_1$–$C_4$ alkyl; R′ and R″ represent the same or different methyl or ethyl; R‴ represents methyl or ethyl and X represents chloro or bromo.

In summary, the reaction of our invention may be represented in the alternative by one of the reaction schemes:

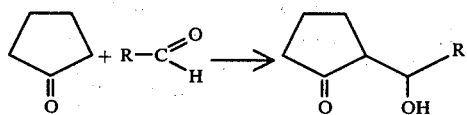

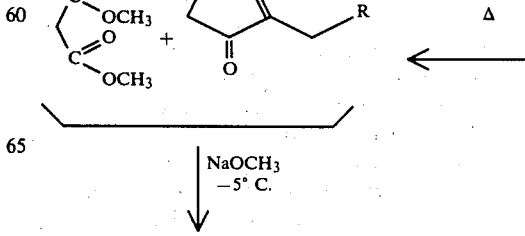

-continued
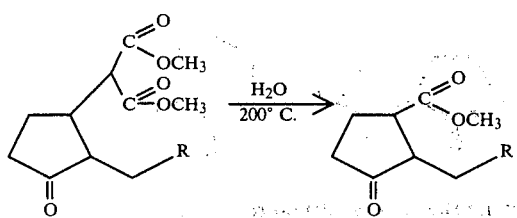
or the reaction scheme:
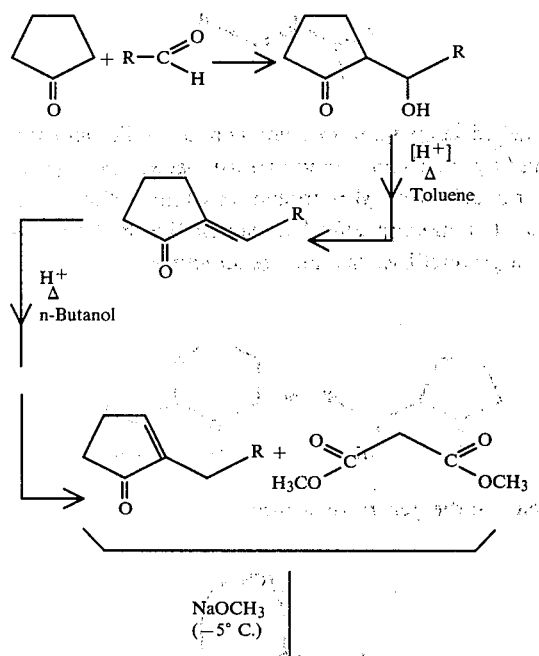
or the reaction scheme:
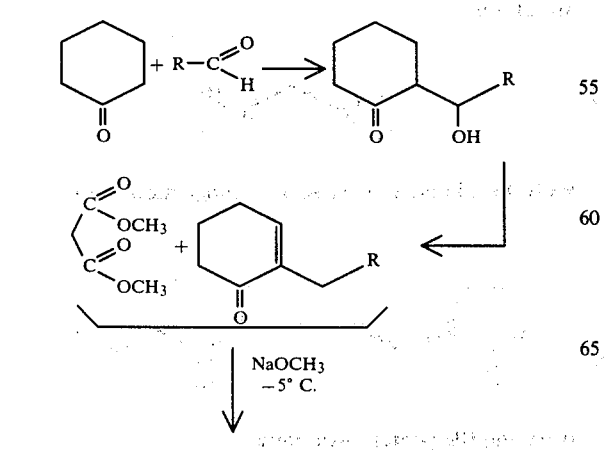
-continued
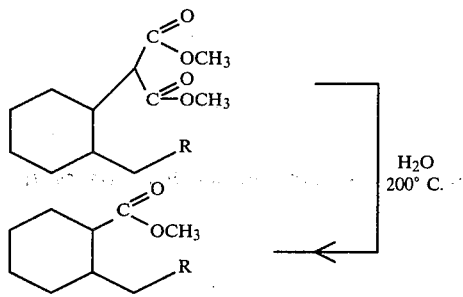
or the reaction scheme:
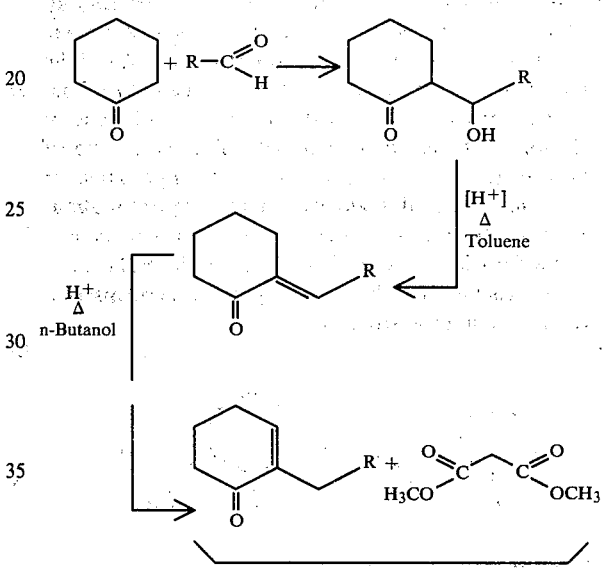
More specifically, the aldol condensation between the cycloalkanone having the structure:
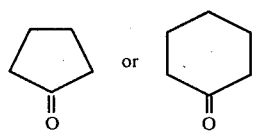
or defined according to the generic structure:

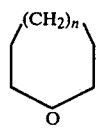

wherein n is 0 or 1 and the aldehyde having the structure:

may take place at a temperature of between 20° and 50° C. over a period of time of from about one half hour up to four hours. Preferably, the reaction time is about one hour and the reaction temperature is about 30° C. The mole ratio of cycloalkanone: aldehyde may vary from about 3:1 up to about 1:3 with a preferred mole ratio of 1.8 moles ketone:1 mole aldehyde. The mole ratio of base used (e.g., sodium hydroxide, barium hydroxide, or potassium hydroxide): aldehyde may vary from about 0.05 moles base: 1 mole aldehyde up to 0.1 mole base: 1 mole aldehyde with a preferred mole ratio of 0.083:1.

The reaction of the resulting aldol condensation product having the structure:

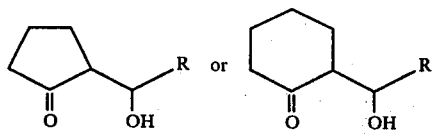

or having the generic structure:

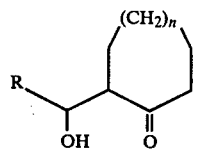

to form, ultimately, the alkyl cyclopentenone having the structure:

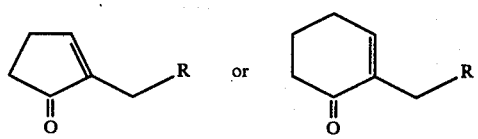

or having the generic structure:

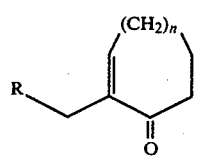

can either be performed stepwise via the alkylidene cyclopentanone having the structure:

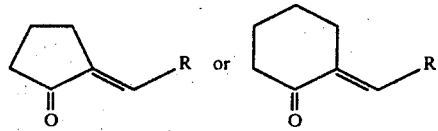

or having the generic structure:

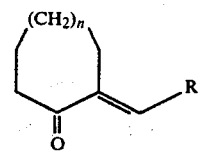

by dehydration with an acid such as oxalic acid followed by endoisomerization with aqueous acid (hydrochloric acid or hydrobromic acid) in refluxing n-butanol or, more specifically, reacting the aldol condensation product itself having the structure:

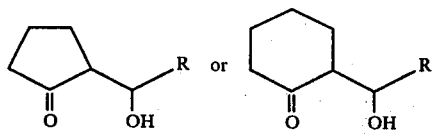

or having the generic structure:

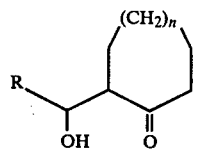

with hydrogen chloride or hydrogen bromide, preferably hydrogen bromide in refluxing n-butanol. As will be seen by the examples, using an acid such as para toluene sulfonic acid fails to give rise to an appreciable yield compared with the use of hydrogen chloride or hydrogen bromide.

The reaction of the malonic acid diester having the structure:

$$R''O-\overset{O}{\underset{}{C}}-CH_2-\overset{O}{\underset{}{C}}-OR'$$

with the alkyl cyclopentenone having the structure:

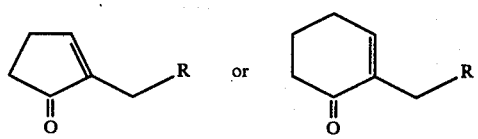

or having the generic structure:

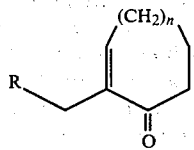

uses ordinary conditions of the Michael Addition synthesis e.g., takes place in the presence of an alkali metal alkoxide such as sodium or potassium methoxide or ethoxide or propoxide at a temperature in the range of from about −20° C. up to about +10° C. with a preferred temperature of about −5° C. The range of conditions may be substantially the same as those described in the analogous reaction in United Kingdom Patent No. 907,431.

The resulting malonic ester-cycloalkenone addition product having one of the structures:

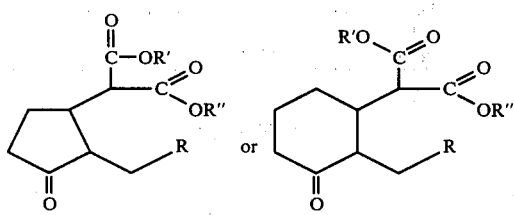

or defined according to the generic structure:

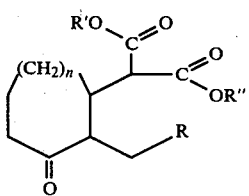

may then be reacted with water at a temperature in the range of from about 180° C. up to about 210° C. at pressures of from about 1 atmosphere up to about 10 atmospheres thereby forming the methyl dihydrojasmonate or homologue thereof defined according to the generic structure:

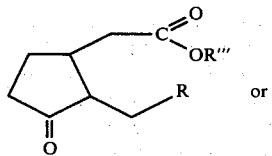 or

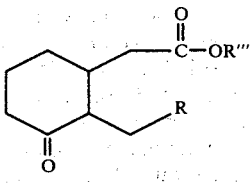

or defined according to the generic structure:

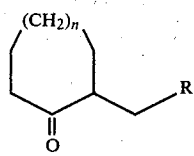

This reaction may be carried out according to the procedures set forth in German Offenlegungsschrift No. 27 32 107 of Jan. 19, 1978.

Alternatively, the malonic ester-cycloalkenone addition product may subsequently be saponified using aqueous alkali metal hydroxide such as sodium hydroxide or potassium hydroxide (20–50% in concentration) and then acidified with hydrochloric acid or acetic acid and finally heated at a temperature in the range of from 150° C. up to 200° C. thereby causing monodecarboxylation of the resulting dicarboxylic acid. The resulting material may then be re-esterified with methanol using a sulfuric acid catalyst according to standard esterification conditions.

The following Examples I–III and V–VII serve to illustrate embodiments of our invention as it is now preferred to practice it. Example IV illustrates the utility for a compound produced according to a process of our invention. It will be understood that these examples are illustrative and restricted thereto only as defined in the appended claims.

EXAMPLE I-A

Reaction:

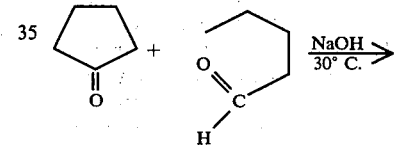

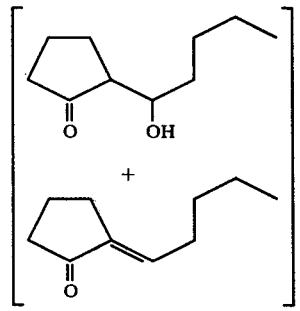

Reaction:

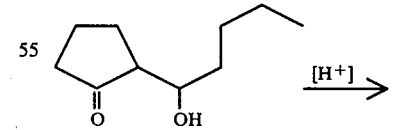

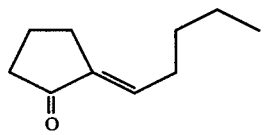

Into a 5-liter reaction flask equipped with mechanical stirrer, 500 ml addition funnel, immersion thermometer and reflux condenser and 5-liter heating mantle and dry ice/isopropyl alcohol bath are charged 16.5 grams of sodium hydroxide and 1500 ml water. The resulting mixture is warmed to 30° C. 756 grams (9.0 moles) of cyclopentanone is then added dropwise with stirring over a 15 minute period while maintaining the reaction temperature at 30° C. with the dry ice/isopropanol bath.

430 grams (5.0 moles) of n-valeraldehyde is then added dropwise with stirring over a 40 minute period while keeping the temperature at 30° C. After addition, the reaction mass is stirred for a period of 1 hour at 30° C.

After 1 hour, 30.0 grams of acetic acid is added using a dropping pipette and the reflux condenser is replaced with a splash column equipped with rush-over head. The resulting mixture is then heated and steam distilled. All fractions are monitored on a 400' SE-30 glass capillary GLC column. The distillation is shut down when no further apparent oil layer is formed. The resulting mixture is allowed to cool down and poured into a separatory funnel. The aqueous layer is separated and washed with two volumes of toluene. The toluene layer is combined with the organic layer and the resulting organic layer is washed with two volumes of saturated sodium chloride solution and then filtered through cotton. The resulting material is placed in the 5-liter reaction flask as equipped above.

10.0 grams of oxalic acid is then added and the reaction mixture is heated with stirring and azeotropically distilling water until no further water is evolved (about 90 ml water being removed). The reaction equipment is then shut down and the reaction mass is cooled and poured into a 4-liter separatory funnel. The reaction mass is then washed with two volumes of saturated sodium chloride solution followed by two volumes of 5% sodium carbonate solution followed by two volumes of saturated sodium chloride solution. The resulting material is then dried over anhydrous sodium sulfate and concentrated to yield 1120.0 grams of material.

The resulting product is then distilled under vacuum using a splash column and rush-over head into 3 fractions with the following results:

| Fraction No. | Weight | % Product | Wt. Product | Vapor Temp. | Liq. Temp. | Press. mm Hg |
|---|---|---|---|---|---|---|
| 1 | 137.2 | 1.2 | 1.60 | 27–38 | 26–106 | 4.40 |
| 2 | 491.4 | 86.3 | 424.1 | 95 | 107 | 0.40 |
| 3 | 162.5 | 90.2 | 146.6 | 106 | 156 | 0.60 |

EXAMPLE I-B

Reaction:

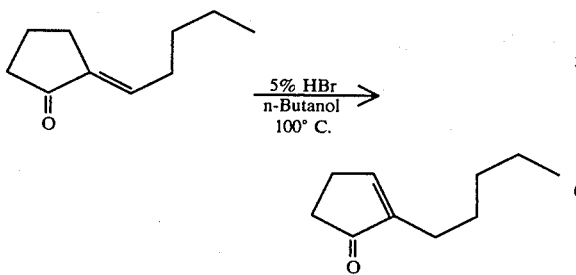

Into a 5-liter reaction flask equipped with mechanical stirrer, immersion thermometer, bubble condenser and 5-liter heating mantle are charged 570.4 grams (3.75 moles) of 2-pentylidene cyclopentanone prepared according to Example I-A (fractions 1–3 bulked) and 2400 ml of 5% hydrogen bromide in n-butanol (120 ml hydrogen bromide in 2280 ml n-butanol). The resulting mixture is heated with stirring to reflux at 105° C. The reaction mass is then stirred over a period of 115 minutes while monitoring the progress on a 6′×¼″ glass SE-30 packed column (operated at 150° C. isothermal) approximately every 5–10 minutes.

After 115 minutes, the reaction apparatus is shut down and the reaction mass is cooled. The resulting mixture is poured into a separatory funnel and washed with 1 volume of saturated sodium chloride solution followed by 1 volume of 10% sodium carbonate solution and 2 volumes of saturated sodium chloride solution. The resulting material is then dried over anhydrous sodium sulfate and concentrated to yield 788.0 grams of crude product. The resulting crude is then distilled under vacuum using a splash column and rush-over head into 3 fractions as follows:

| Fraction No. | Weight | % Product | Wt. Product | Vapor Temp. | Liq. Temp. | Press. mm Hg |
|---|---|---|---|---|---|---|
| 1 | 138.85 | 4.68 | 6.50 | 26–35 | 28–90 | 1.30 |
| 2 | 259.92 | 90.43 | 235.05 | 81 | 102 | 1.35 |
| 3 | 224.40 | 86.72 | 194.60 | 87 | 174 | |

EXAMPLE I-C

Reaction:

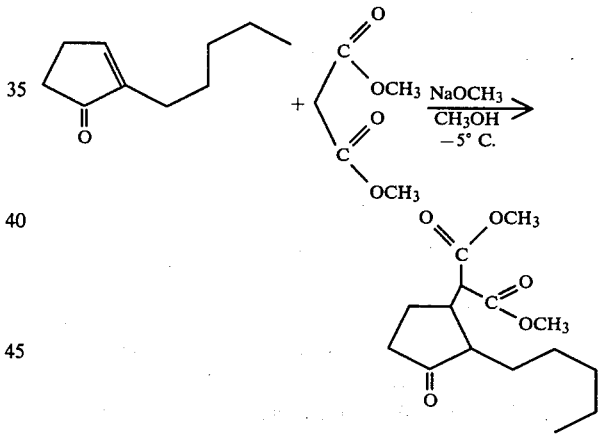

Into a 5-liter reaction flask equipped with mechanical stirrer, immersion thermometer, 1000 ml addition funnel with nitrogen inlet and water-cooled condenser with nitrogen bubbler and dry ice/isopropyl alcohol bath is placed 1350 ml of anhydrous methyl alcohol and 7.82 grams (0.34 gm-atoms) of sodium pellets under a nitrogen atmosphere at 25° C. In one batch, 448.8 grams (3.40 moles) of dimethyl malonate is added with stirring while maintaining the reaction mass temperature at 25° C. The reaction mass is then cooled to −5° C.

Over a 40 minute period 429.65 grams (2.83 moles) of 2-pentyl-2-cyclopent-1-one prepared according to Example I-B is added. The reaction mass is then stirred for a period of 1 hour at −5° C. 40.8 grams (0.68 moles) of acetic acid is then added to the reaction mass and the reaction mixture is stirred and permitted to attain room temperature. The reaction mass is then transferred to a large separatory funnel. Approximately 2 liters of water is added to the reaction mass and the resulting mixture is shaken vigorously. The oil layer separates to the bottom and is removed and retained.

The aqueous layer is then stripped to remove the methanol; washed with 2 volumes of diethyl ether and discarded. The diethyl ether washings are combined with the organic layer (the oil layer), washed two times with saturated sodium chloride solution and then dried over anhydrous sodium sulfate. The resulting dried material is concentrated to yield 1271 grams of crude material. GLC analysis on a 6'×¼" SE-30 packed glass column shows the crude to be 40.34% diester (512.72 grams=63.79% yield).

EXAMPLE I-D

Reaction:

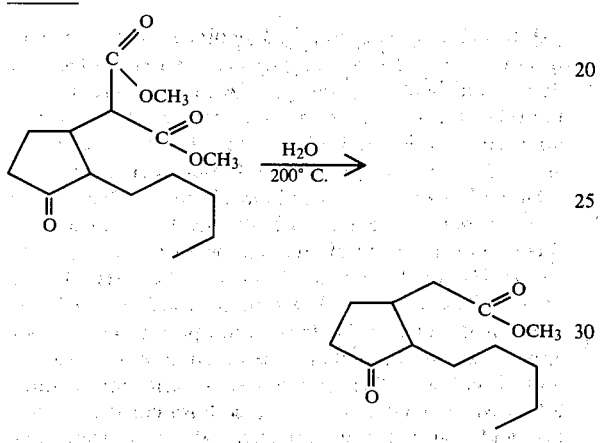

Into a 3-liter reaction flask equipped with mechanical stirrer, immersion thermometer, 250 ml addition funnel with nitrogen inlet, 1-ft. jacketed column packed with saddles, a rush-over head with thermometer, a take-off adapter with nitrogen bubbler, a 500 ml receiver and a heating mantle is placed 1271.0 grams of the crude 3-dimethylmalonyl-2-pentylcyclopent-1-one prepared according to Example I-C. The compound is heated with stirring to 200° C. During the heating, any solvent from the previous reaction of Example I-C distills over and is discarded. At 200° C., 50.94 grams (2.83 moles) of water is added dropwise (1 drop per 1.5 seconds) causing a vigorous evolution of carbon dioxide and methyl alcohol which is collected in the receiver. The addition takes approximately 1 hour. Heating at 200° C. is continued for 35 minutes. The reaction is monitored by GLC (6'×¼" SE-30 packed glass column) immediately after the water addition and 35 minutes later. Substantial diester still remains so an additional 10 grams of water is added over a 20 minute period and the reaction mass is again stirred for 30 minutes. GLC analysis continues to show diester as the reaction is shut down for 12 hours and recommenced when an additional 10 grams of water is added at 200° C. over a 20 minute period. Stirring is continued at 200° C. for an additional 30 minutes. At this point, GLC analysis indicates no diester is present and the reaction apparatus is shut down and the reaction mass cooled to room temperature.

The crude material (664 grams) is then distilled under vacuum on a 2" splash column with rush-over head into four fractions as follows:

| Fraction No. | Weight | % Product | Wt. Product | Vapor Temp. | Liq. Temp. | Press. mm Hg |
|---|---|---|---|---|---|---|
| 1 | 64.07 | 4.67 | 2.99 | 112 | 134 | 0.35 |
| 2 | 239.66 | 75.04 | 179.84 | 112 | 134 | 0.35 |
| 3 | 306.74 | 98.33 | 301.62 | 112 | 136–139 | 0.30–0.33 |
| 4 | 28.30 | 89.77 | 25.41 | 112 | 148–200 | 0.30 |

Fractions 2, 3 and 4 are bulked and fractionally distilled on a 12" Hemple Column having Goodloe packing. The distillation is such that the material is distilled into 11 fractions as follows:

| Fraction No. | Weight | % Product | Wt. Product | Vapor Temp. | Liq. Temp. | Press. mm Hg | Reflux Ratio |
|---|---|---|---|---|---|---|---|
| 1 | 13.37 |  |  | 51–53 | 125–136 | 0.19 | 4:1 |
| 2 | 18.22 |  |  | 58 | 137.5 | 0.15 | 4:1 |
| 3 | 5.43 |  |  | 85 | 138 | 0.18 | 4:1 |
| 4 | 17.62 | 93.58 | 16.49 | 80–103 | 137–140 | 0.16 | 4:1 |
| 5 | 12.02 | 98.35 | 11.82 | 101 | 146 | 0.16 | 4:1 |
| 6 | 72.75 | 99.41 | 72.32 | 105 | 152 | 0.16 | 1:1 |
| 7 | 77.05 | 99.52 | 76.68 | 108 | 156 | 0.16 | 1:1 |
| 8 | 105.63 | 99.49 | 105.09 | 109 | 159 | 0.16 | 1:1 |
| 9 | 77.33 | 99.44 | 76.90 | 109 | 162 | 0.16 | 1:1 |
| 10 | 96.83 | 98.56 | 95.44 | 109 | 182 | 0.16 | 1:1 |
| 11 | 37.90 | 90.88 | 34.44 | 139 | 220 | 0.16 | 1:1 |

EXAMPLE II-A

Reaction:

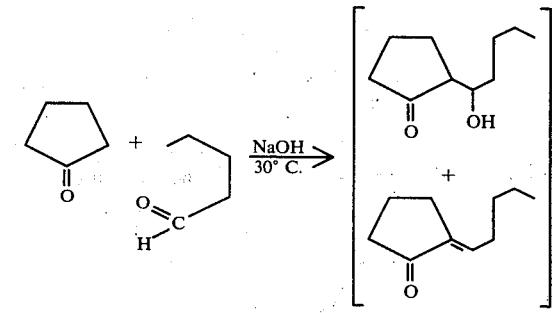

Into a 500 ml reaction flask equipped with mechanical stirrer, immersion thermometer, 150 ml addition funnel, water-cooled condenser, heating mantle and ice bath is placed 1.65 grams of sodium hydroxide pellets and 155 ml water. The resulting solution is warmed to 30° C. 75.6 grams (0.9 moles) of cyclopentanone is then added dropwise with stirring while maintaining the temperature at 30°–31° C. 43.0 grams (0.5 moles) of n-valeraldehyde is then added dropwise with stirring over a period of about 30 minutes while maintaining the temperature at 30° C. The reaction mass is then stirred for 1 hour at 30° C. At this point, 3.0 grams of acetic acid and 100 ml of water are added. The condenser is then replaced with a splash column and rush-over head and the reaction mass is heated to 95° C. to distill the unreacted cyclopentanone. The reaction mass is then distilled until the head temperature is 100° C. and the majority of the cyclopentanone is recovered. The reaction apparatus is then shut down and the reaction mass is cooled and poured into a separatory funnel.

The oil layer is taken up in diethyl ether and separated from the aqueous layer. It is then washed with 1 volume of saturated sodium chloride solution and dried over anhydrous sodium sulfate and concentrated to yield 77.46 grams of crude product.

EXAMPLE II-B

Reaction:

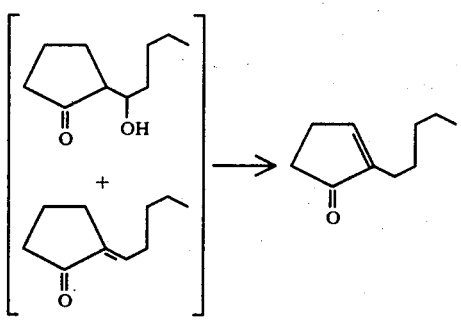

Into a 250 ml reaction flask equipped with mechanical stirrer, immersion thermometer, water-cooled condenser and heating mantle are charged 38.73 grams (0.23 moles) of the aldol condensation product produced according to Example II-A and 138.6 ml of 5% hydrogen bromide in n-butanol (6.60 ml of 48% of HBR in 132 ml n-butanol). The reaction mixture is heated to reflux (102° C.) and maintained at reflux (monitoring by GLC) until all of the isomer having the structure:

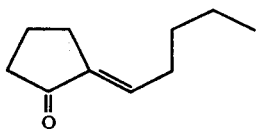

is isomerized to the product having the structure:

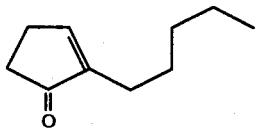

in a ratio of 14:1 endo:exo (87.9% endo:6.3% exo). The reaction apparatus is then shut down and the reaction mass is cooled and poured into a separatory funnel. The oil layer is then washed with 1 volume of saturated sodium chloride solution; followed by 1 volume of 10% sodium carbonate solution; followed by 3 volumes of saturated sodium chloride solution. The resulting material is then dried over anhydrous sodium sulfate and the crude material (186.61 grams) is distilled under vacuum into 2 fractions as follows:

| Fraction No. | Weight | % Product | Wt. Product | Vapor Temp. | Liq. Temp. | Press. mm Hg |
|---|---|---|---|---|---|---|
| 1 | 155.8 | 0.29 | 0.45 | 20–22 | 85–90 | 1.6 |
| 2 | 20.3 | 85.25 | 17.31 | 75 | 135 | 1.6 |

Yield of product is 17.76 grams (50.80%).

EXAMPLE II-C

Reaction:

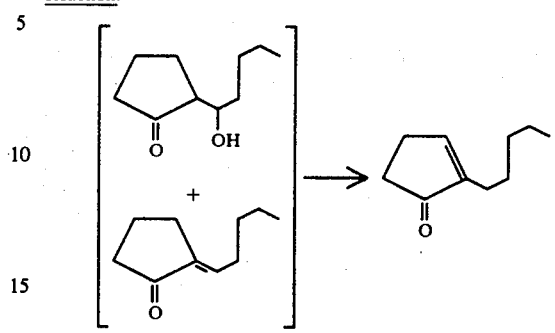

Into a 250 ml reaction flask equipped with mechanical stirrer, immersion thermometer, water-cooled condenser and heating mantle is placed 38.73 grams (0.23 moles) of the aldol condensation product of cyclopentanone and n-valeraldehyde produced according to Example II-A and 176.4 ml of 5% hydrogen chloride in n-butanol (8.4 ml of 38% HCl in 168 ml n-butanol). The reaction mass is heated with stirring to reflux and refluxed until the ratio of endo:exo isomer is 13:1 (87.4% endo:6.7% exo) monitored on a 6'×¼" SE-30 glass packed GLC column). The time of reaction is 165 minutes. At the end of the 165-minute period the reaction apparatus is shut down and the reaction mass is washed with 1 volume of saturated sodium chloride solution followed by 1 volume of 10% sodium carbonate solution and 3 volumes of saturated sodium chloride solution. The product is then dried over anhydrous sodium sulfate to yield 249 grams of crude. The crude material is distilled under vacuum over a rush-over head as follows:

| Fraction No. | Weight | % Product | Wt. Product | Vapor Temp. | Liq. Temp. | Press. mm Hg |
|---|---|---|---|---|---|---|
| 1 | 142.63 | 0.44 | 0.63 | 20–22 | 82–85 | 1.5 |
| 2 | 19.45 | 87.57 | 17.03 | 56 | 185 | 0.40 |

Yield of product is 17.66 grams (50.52%).

EXAMPLE II-D

Attempted Reaction:

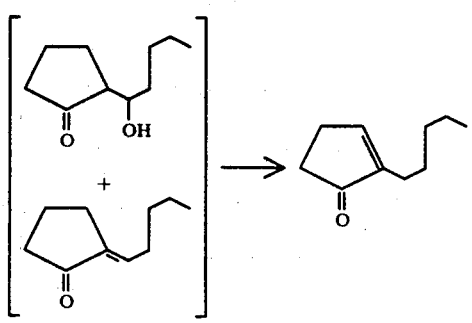

Into a 250 ml reaction flask equipped with mechanical stirrer, Dean-Stark trap with Friedrich's condenser, immersion thermometer and heating mantle is placed 20.0 grams (0.12 moles) of the cyclopentanone-n-valeraldehyde aldol condensation product produced according to Example II-A; 100 ml toluene and 2.28 grams (0.012 moles) of paratoluene sulfonic acid. The reaction mass is heated to reflux (114° C.) with stirring and approximately 2.6 ml water was azeotropically distilled from the reaction mass. The reaction is carried on for about 140 minutes and then the apparatus is shut down overnight for a period of 12 hours. The reaction is then restarted and run for 120 minutes additional time. The reaction mass is monitored on a 6'×¼" SE-30 GLC column until sufficient conversion appears to take place (91.6% endo:3.7% exo). The apparatus is shut down and the reaction product is cooled to room temperature.

The reaction product is washed with 1 volume of saturated sodium chloride solution; 2 volumes of 5% sodium carbonate solution; and 2 volumes of saturated sodium chloride solution. The product is then dried over anhydrous sodium sulfate and concentrated to yield 15.46 grams of crude material. The crude is then rush-over distilled under vacuum into fractions as follows:

| Fraction No. | Weight | % Product | Wt. Product | Vapor Temp. | Liq. Temp. | Press. mm Hg |
|---|---|---|---|---|---|---|
| 1 | 1.22 | 90.99 | 1.11 | 25–26 | 28–205 | 0.95 |

Yield of product 1.11 grams (6.09%).

EXAMPLE III

Reaction:

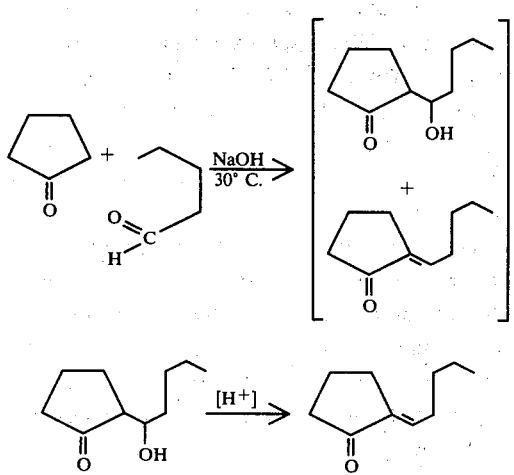

Into a 5-liter reaction flask equipped with mechanical stirrer, 500 ml addition funnel, immersion thermometer, Friedrich's condenser, heating mantle and dry ice/isopropyl alcohol bath are placed 1.5 liters of water and 16.5 grams of sodium hydroxide. The resulting solution is warmed to 30° C. 756 grams (9.0 moles) of cyclopentanone is added dropwise with stirring while maintaining the temperature at 30° C. After addition of the cyclopentanone, 430 grams (5.0 moles) of n-valeraldehyde was added dropwise with stirring keeping the temperature at 30° C. using the isopropyl alcohol/dry ice bath as needed. The reaction mass is then stirred for a period of 1 hour at 30° C.

After 1 hour, 30.0 grams of acetic acid is added from a dropping pipette while maintaining the temperature of 30° C. and stirring the reaction mass for 2–3 minutes thus obtaining in the reaction mass a pH of 6. The reaction apparatus is then shut down and the reaction mass is poured into a separatory funnel where the water and oil layers are separated. The water layer is washed with 2 volumes of toluene and the toluene layer is combined with the oil layer and the washed aqueous layer is discarded. The organic layer is then washed with 2 volumes of saturated sodium chloride solution and filtered through cotton. The resulting organic material is then charged into a 5-liter reaction flask equipped with mechanical stirrer, Bidwell trap with bubble condenser, immersion thermometer and heating mantle and 10.0 grams of oxalic acid is added to the reaction mass. The resulting mixture is heated to reflux with stirring and water is azeotropically distilled until no further water is evolved (about 9 hours). 95 ml water is recovered. The resulting mixture is then cooled to room temperature and poured into a separatory funnel. The organic layer is washed with 2 volumes of saturated sodium chloride solution followed by 1 volume of 5% sodium carbonate solution, followed by 2 volumes of saturated sodium chloride solution. The resulting organic material is dried over anhydrous sodium sulfate and concentrated to yield 582 grams of crude product. This material is distilled in vacuo using a 2" splash column and rush-over head into five fractions as follows:

| Fraction No. | Weight | % Product | Wt. Product | Vapor Temp. | Liq. Temp. | Press. mm Hg |
|---|---|---|---|---|---|---|
| 1 | 201.94 | 1.31 | 2.65 | 27–32 | 38–109 | 2.80 |
| 2 | 159.85 | 90.59 | 144.81 | 27 | 94 | 0.22 |
| 3 | 252.28 | 93.75 | 236.51 | 26–80 | 26–107 | 0.24 |
| 4 | 225.34 | 86.94 | 195.91 | 93 | 149 | 0.43 |
| 5 | 15.88 | 17.06 | 2.71 | 100 | 170 | 0.43 |

Yield of product is 582.59 grams (76.66%).

EXAMPLE IV

Jasmine Perfume

The following mixture is prepared:

| Ingredient | Parts by Weight |
|---|---|
| Para Cresol | 1 |
| Acetyl Methyl Anthranilate | 20 |
| Farnesol | 4 |
| Cis-3-hexenyl benzoate | 30 |
| Nerolidol | 30 |
| Indol | 15 |
| Eugenol | 20 |
| Benzyl Alcohol | 40 |
| Methyl Linoleate | 40 |
| Jasmin Lactone | 20 |
| Dihydromethyl Jasmonate | 10 |
| Linalool | 150 |
| Benzyl Acetate | 400 |
| Abietyl Alcohol | 150 |
| Methyl dihydrojasmonate (Produced according to Example I-D; bulked fractions 5–10) | 50 |

The methyl dihydrojasmonate produced according to Example I-D imparts to this jasmine formulation the green, sweet, floral note so important to the jasmine perfume formulation.

EXAMPLE V-A

Reaction:

-continued

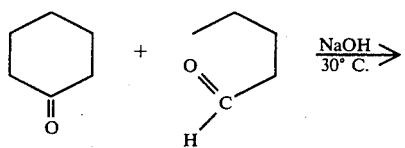

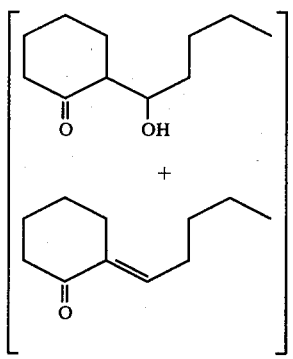

Reaction:

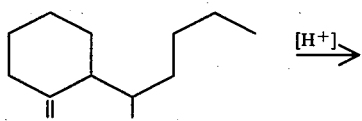

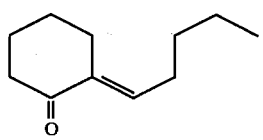

Into a 5-liter reaction flask equipped with mechanical stirrer, 500 ml addition funnel, immersion thermometer and reflux condenser and 5-liter heating mantle and dry ice/isopropyl alcohol bath are charged 16.5 grams of sodium hydroxide and 1500 ml water. The resulting mixture is warmed to 30° C. 882 grams (9.0 moles) of cyclohexanone is then added dropwise with stirring over a 15 minute period while maintaining the reaction temperature at 30° C. with the dry ice/isopropanol bath.

430 grams (5.0 moles) of n-valeraldehyde is then added dropwise with stirring over a 40 minute period while keeping the temperature at 30° C. After addition, the reaction mass is stirred for a period of 1 hour at 30° C.

After 1 hour, 30.0 grams of acetic acid is added using a dropping pipette and the reflux condenser is replaced with a splash column equipped with rush-over head. The resulting mixture is then heated and steam distilled. All fractions are monitored on a 400′ SE-30 glass capillary GLC column. The distillation is shut down when no further apparent oil layer is formed. The resulting mixture is allowed to cool down and poured into a separatory funnel. The aqueous layer is separated and washed with two volumes of toluene. The toluene layer is combined with the organic layer and the resulting organic layer is washed with two volumes of saturated sodium chloride solution and then filtered through cotton. The resulting material is placed in the 5-liter reaction flask as equipped above.

10.0 grams of oxalic acid is then added and the reaction mixture is heated with stirring and azeotropically distilling water until no further water is evolved (about 90 ml water being removed). The reaction equipment is then shut down and the reaction mass is cooled and poured into a 4-liter separatory funnel. The reaction mass is then washed with two volumes of saturated sodium chloride solution followed by two volumes of 5% sodium carbonate solution followed by two volumes of saturated sodium chloride solution. The resulting material is then dried over anhydrous sodium sulfate and concentrated to yield 1120.0 grams of material.

The resulting product is then distilled under vacuum using a splash column and rush-over head.

EXAMPLE V-B

Reaction:

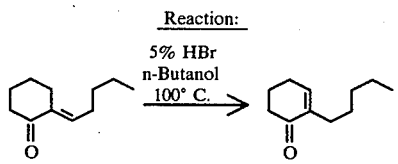

Into a 5-liter reaction flask equipped with mechanical stirrer, immersion thermometer, bubble condenser and 5-liter heating mantel are charged 581.3 grams (3.75 moles) of 2-pentylidene cyclohexanone prepared according to Example V-A and 2400 ml of 5% hydrogen bromide in n-butanol (120 ml hydrogen bromide in 2280 ml n-butanol). The resulting mixture is heated with stirring to reflux at 105° C. The reaction mass is then stirred over a period of 115 minutes while monitoring the progress on a 6′×¼″ glass SE-30 packed column (operated at 150° C. isothermal) approximately every 5–10 minutes.

After 115 minutes, the reaction apparatus is shut down and the reaction mass is cooled. The resulting mixture is poured into a separatory funnel and washed with 1 volume of saturated sodium chloride solution followed by 1 volume of 10% sodium carbonate solution and 2 volumes of saturated sodium chloride solution. The resulting material is then dried over anhydrous sodium sulfate and concentrated to yield 795 grams of crude product. The resulting crude is then distilled under vacuum using a splash column and rush-over head.

EXAMPLE V-C

Reaction:

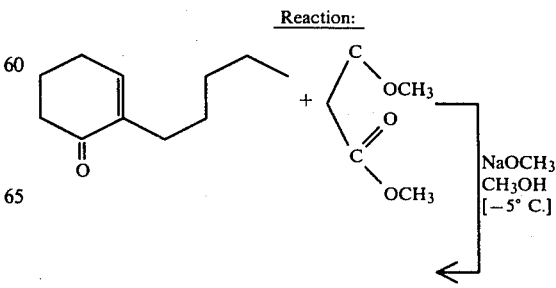

-continued
Reaction:

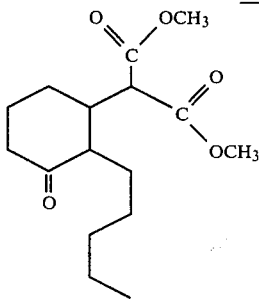

Into a 5-liter reaction flask equipped with mechanical stirrer, immersion thermometer, 1000 ml addition funnel with nitrogen inlet and water-cooled condenser with nitrogen bubbler and dry ice/isopropyl alcohol bath is placed 1350 ml of anhydrous methyl alcohol and 7.82 grams (0.34 gm-atoms) of sodium pellets under a nitrogen atmosphere at 25° C. In one batch, 448.8 grams (3.40 moles) of dimethyl malonate is added with stirring while maintaining the reaction mass temperature at 25° C. The reaction mass is then cooled to −5° C.

Over a 40 minute period 492 grams (3.00 moles) of 2-pentyl-2-cyclohexen-1-one prepared according to Example V-B is added. The reaction mass is then stirred for a period of 1 hour at −5° C. 40.8 grams (0.68 moles) of acetic acid is then added to the reaction mass and the reaction mixture is stirred and permitted to attain room temperature. The reaction mass is then transferred to a large separatory funnel. Approximately 2 liters of water is added to the reaction mass and the resulting mixture is shaken vigorously. The oil layer separates to the bottom and is removed and retained.

The aqueous layer is then stripped to remove the methanol; washed with 2 volumes of diethyl ether and discarded. The diethyl ether washings are combined with the organic layer (the oil layer), washed two times with saturated sodium chloride solution and then dried over anhydrous sodium sulfate. The resulting dried material is concentrated to yield 1271 grams of crude material. GLC analysis on a 6′×¼″ SE-30 packed glass column shows the crude to be 40.34% diester (512.72 grams=63.79% yield).

EXAMPLE 5-D

Reaction:

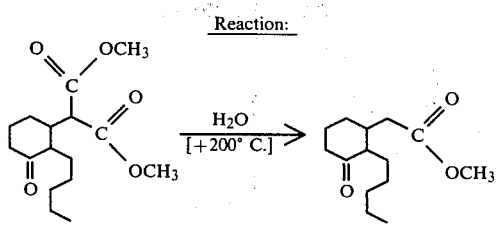

Into a 3-liter reaction flask equipped with mechanical stirrer, immersion thermometer, 250 ml addition funnel with nitrogen inlet, 1-ft. jacketed column packed with saddles, a rush-over head with thermometer, a take-off adapter with nitrogen bubbler, a 500 ml receiver and a heating mantle is placed 1280.0 grams of the crude 3-dimethylmalonyl-2-pentylcyclohexan-1-one prepared according to Example V-C. The compound is heated with stirring to 200° C. During the heating, any solvent from the previous reaction of Example V-C distills over and is discarded. At 200° C., 50.94 grams (2.83 moles) of water is added dropwise (1 drop per 1.5 seconds) causing a vigorous evolution of carbon dioxide and methyl alcohol which is collected in the receiver. The addition takes approximately 1 hour. Heating at 200° C. is continued for 35 minutes. The reaction is monitored by GLC (6′×¼″ SE-30 packed glass column) immediately after the water addition and 35 minutes later. Substantial diester still remains so an additional 10 grams of water is added over a 20 minute period and the reaction mass is again stirred for 30 minutes. GLC analysis continues to show diester as the reaction is shut down for 12 hours and recommenced when an additional 10 grams of water is added at 200° C. over a 20 minute period. Stirring is continued at 200° C. for an additional 30 minutes. At this point, GLC analysis indicates no diester is present and the reaction apparatus is shut down and the reaction mass cooled to room temperature.

The crude material (640 grams) is then distilled under vacuum on a 2″ splash column with rush-over head. The resulting fractions are then fractionally distilled on a 12″ Hemple Column having a Goodloe packing. The distillation yields the resulting product in 11 fractions.

EXAMPLE VI-A

Reaction:

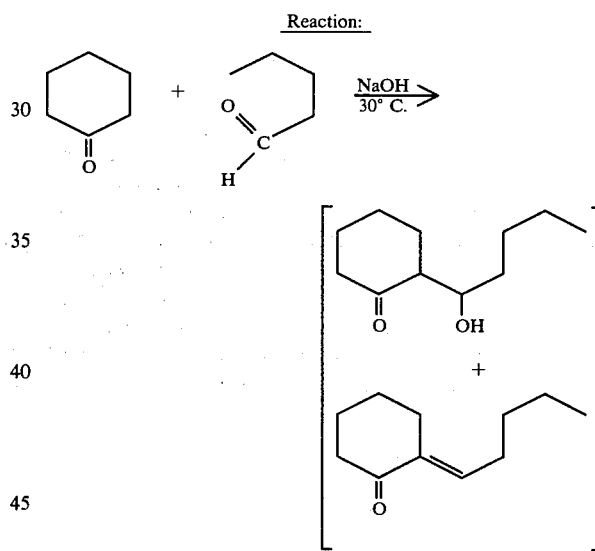

Into a 500 ml reaction flask equipped with mechanical stirrer, immersion thermometer, 150 ml addition funnel, water-cooled condenser, heating mantle and ice bath is placed 1.65 grams of sodium hydroxide pellets and 155 ml water. The resulting solution is warmed to 30° C. 75.6 grams (0.9 moles) of cyclohexanone is then added dropwise with stirring while maintaining the temperature at 30°-31° C. 43.0 grams (0.5 moles) of n-valeraldehyde is then added dropwise with stirring over a period of about 30 minutes while maintaining the temperature at 30° C. The reaction mass is then stirred for 1 hour at 30° C. At this point, 3.0 grams of acetic acid and 100 ml of water are added. The condenser is then replaced with a splash column and rush-over head and the reaction mass is heated to 95° C. to distill the unreacted cyclohexanone. The reaction mass is then distilled until the head temperature is 100° C. and the majority of the cyclohexanone is removed. The reaction apparatus is then shut down and the reaction mass is cooled and poured into a separatory funnel.

The oil layer is taken up in diethyl ether and separated form the aqueous layer. It is then washed with 1 volume of saturated sodium chloride solution and dried over anhydrous sodium sulfate and concentrated to yield 72.52 grams of crude product.

EXAMPLE VI-B

Reaction:

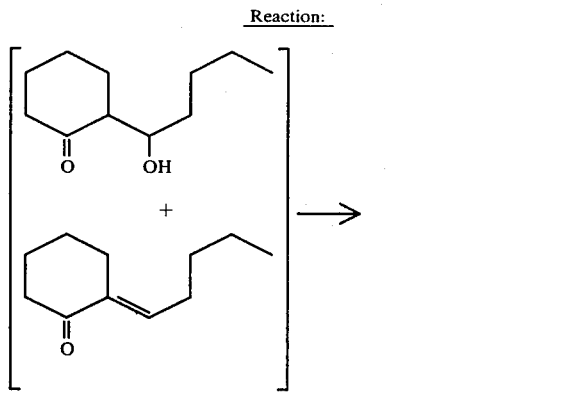

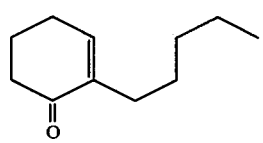

Into a 250 ml reaction flask equipped with mechanical stirrer, immersion thermomether, water-cooled condenser and heating mantel are charged 0.25 moles of the aldol condensation product produced according to Example VI-A and 138.6 ml of 5% hydrogen bromide in n-butanol (6.60 ml of 48% of HBr in 132 ml of n-butanol). The reaction mixture is heated to reflux (102° C.) and maintained at reflux (monitoring by GLC until all of the isomer having the structure:

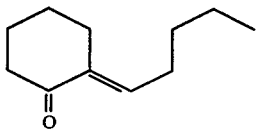

is isomerized to the product having the structure:

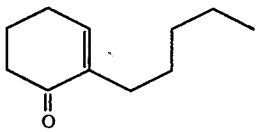

The ratio of endo:exo is about 14:1. The reaction apparatus is then shut down and the reaction mass is cooled and poured into a separatory funnel. The oil layer is then washed with 1 volume of saturated sodium chloride solution; followed by 1 volume of 10% sodium carbonate solution; followed by 3 volumes of saturated sodium chloride solution. The resulting material is then dried over anhydrous sodium sulfate and the crude material (172 grams) is distilled under vacuum. The yield is 140 grams.

EXAMPLE VI-C

Reaction:

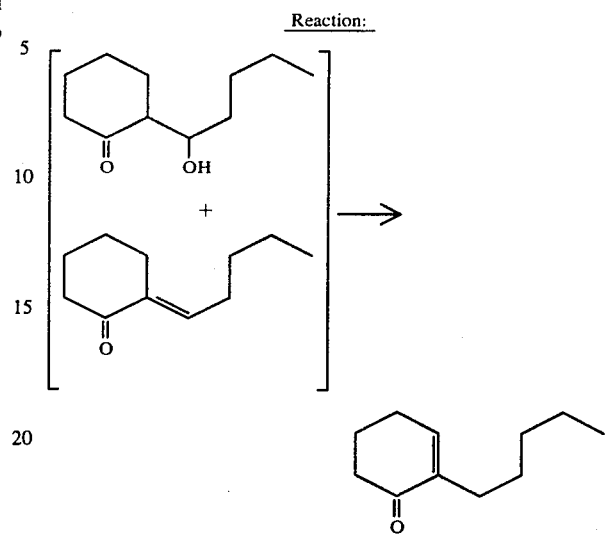

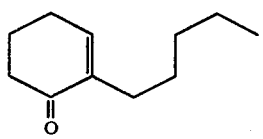

Into a 250 ml reaction flask equipped with mechanical stirrer, immersion thermometer, water-cooled condenser and heating mantle is placed 0.23 moles of the aldol condensation product of cyclohexanone and n-valeraldehyde produced according to Example VI-A and 176.4 ml of 5% hydrogen chloride in n-butanol (8.4 ml of 38% HCl in 168 ml n-butanol). The reaction mass is heated with stirring to reflux and refluxed until a ratio of endo:exo isomer is about 13:1 monitored on a 6'×¼" SE-30 glass packed GLC column. The time of reaction of 170 minutes. At the end of the 170-minute period the reaction apparatus is shut down and the reaction mass is washed with 1 volume of saturated sodium chloride solution followed by 1 volume of 10% sodium carbonate solution and 3 volumes of saturated sodium chloride solution. The product is then dried over anhydrous sodium sulfate to yield 230 grams of crude. The crude material is distilled under vacuum using a rush-over head. The yield of product is 140 grams.

EXAMPLE VI-D

Attempted Reaction:

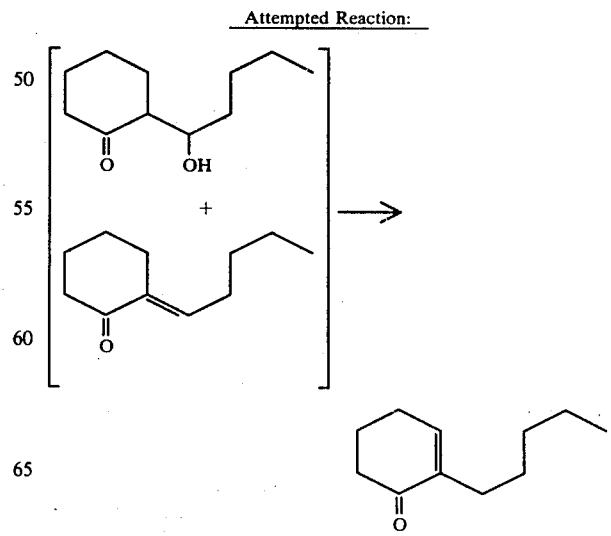

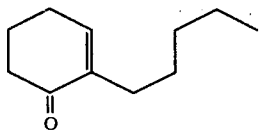

Into a 250 ml reaction flask equipped with mechanical stirrer, Dean-Stark trap with Freidrich's condenser, immersion thermometer and heating mantle is placed 20.0 grams of the cyclohexanone-n-valeraldehyde aldol condensation product produced according to Example VI-A; 100 ml toluene and 2.28 grams (0.012 moles) of paratoluene sulfonic acid. The reaction mass is heated to reflux (114° C.) with stirring and approximately 2.6 ml water is azeotropically distilled from the reaction mass. The reaction is carried on for about 140 minutes and then the apparatus is shut down overnight for a period of 12 hours. The reaction is then restarted and run for 120 minutes additional time. The reaction mass is monitored on a 6'×¼" SE-30 GLC column until sufficient conversion appears to take place (about 13:1 endo:exo). The apparatus is shut down and the reaction product is cooled to room temperature.

The reaction product is washed with 1 volume of saturated sodium chloride solution; 2 volumes of 5% sodium carbonate solution; and 2 volumes of saturated sodium chloride solution. The product is then dried over anhydrous sodium sulfate and concentrated to yield 20.0 grams of crude material. The crude product is then rush-over distilled under vacuum yielding 11.1 grams of final product.

EXAMPLE VII

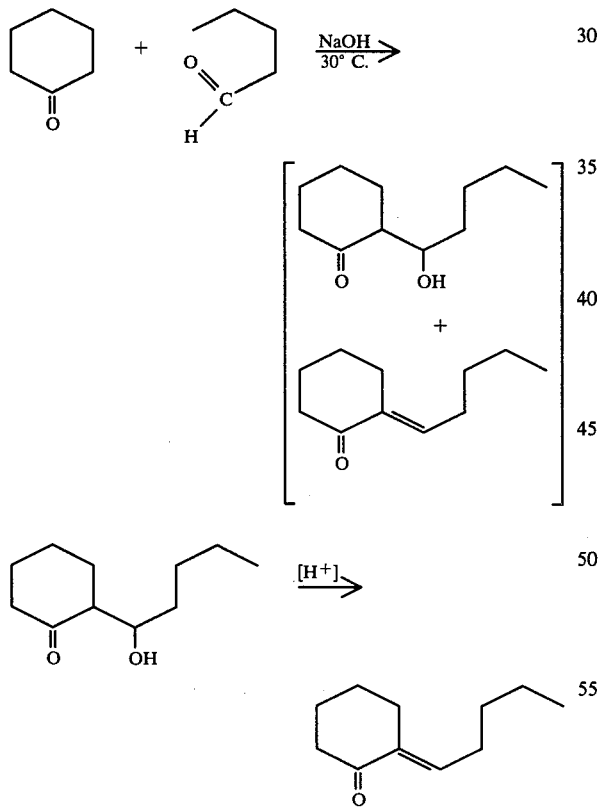

Into a 5-liter reaction flask equipped with mechanical stirrer, 500 ml addition funnel, immersion thermometer, Friedrich's condenser, heating mantel and dry ice/isopropyl alcohol bath are placed 1.5 liter of water and 16.5 grams of sodium hydroxide. The resulting solution is warmed to 30° C. 9.0 moles of cyclohexanone is added dropwise with stirring while maintaining the temperature at 30° C. After addition of the cyclohexanone, 430 grams (5.0 moles) of n-valeraldehyde is added dropwise with stirring keeping the temperature at 30° C. using the isopropyl alcohol/dry ice bath as needed. The reaction mass is then stirred for a period of 1 hour at 30° C.

After 1 hour, 30.0 grams of acetic acid is added from a dropping pipette while maintaining the temperature at 30° C. and stirring the reaction mass for 2-3 minutes thus obtaining in the reaction mass a pH of 6.

The reaction apparatus is then shut down and the reaction mass is poured into a separatory funnel where the water and oil layers are separated. The water layer is washed with 2 volumes of toluene and the toleune layer is combined with the oil layer and the washed aqueous layer is discarded. The organic layer is then washed with 2 volumes of saturated sodium chloride solution and filtered through cotton. The resulting organic material is then charged into a 5-liter reaction flask equipped with mechanical stirrer, Bidwell trap with bubble condenser, immersion thermometer and heating mantle and 10.0 grams of oxalic acid is added to the reaction mass. The resulting mixture is heated to reflux with stirring and water is azeotropically distilled until no further water is evolved (about 9 hours). 95 ml water is recovered. The resulting mixture is then cooled to room temperature and poured into a separatory funnel. The organic layer is washed with 2 volumes of saturated sodium chloride solution followed by 1 volume of 5% sodium carbonate solution, followed by 2 volumes of saturated sodium chloride solution. The resulting organic material is dried over anhydrous sodium sulfate and concentrated to yield 485 grams of crude product. This material is distilled in vacuo using a 2" splash column and rush-over head. The yield of product is 375 grams.

What is claimed is:

1. The process of reacting the compound having the structure:

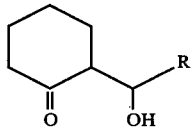

with HX in the presence of n-butanol or toluene in order to form, in one step, a compound having the structure:

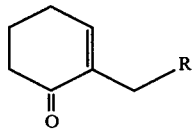

wherein R is $C_1$-$C_4$ alkyl and X is chloro or bromo.

2. The process of claim 1 wherein R is n-butyl.

3. The process of claim 2 wherein X is bromo.

4. The process of claim 2 wherein the solvent used is n-butanol.

5. The process of claim 2 wherein the solvent used is toluene.

* * * * *